US010955506B2

(12) United States Patent
Peeters et al.

(10) Patent No.: US 10,955,506 B2
(45) Date of Patent: Mar. 23, 2021

(54) PARALLEL MR IMAGING WITH SPECTRAL FAT SUPPRESSION

(71) Applicant: KONINKLIJKE PHILIPS N.V., Eindhoven (NL)

(72) Inventors: Johannes Martinus Peeters, Nuenen (NL); Elwin De Weerdt, Tilburg (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/293,718

(22) Filed: Mar. 6, 2019

(65) Prior Publication Data

US 2019/0277934 A1   Sep. 12, 2019

(30) Foreign Application Priority Data

Mar. 9, 2018  (EP) ..................................... 18160893

(51) Int. Cl.
*G01V 3/00* (2006.01)
*G01R 33/561* (2006.01)
(Continued)

(52) U.S. Cl.
CPC .... *G01R 33/5611* (2013.01); *G01R 33/34015* (2013.01); *G01R 33/443* (2013.01); (Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS 5,578,921 A * 11/1996 Morrell ................ G01R 33/446
324/307
9,664,761 B2   5/2017 Liu
(Continued)

FOREIGN PATENT DOCUMENTS

EP         2503348 A1    9/2012

OTHER PUBLICATIONS

Mukherjee et al "Develoment and Initial Evaluation of 7-T Q-Ball Imaging of the Human Brain" Mgnetic Resonance Imaging, vol. 26, No. 2, Jan. 29, 2008 p. 171-180.

*Primary Examiner* — Walter L Lindsay, Jr.
*Assistant Examiner* — Frederick Wenderoth

(57) ABSTRACT

A magnetic resonance (MR) imaging technique enables parallel imaging in combination with fat suppression at an increased image quality, notably in combination with EPI. The method includes acquiring reference MR signal data from the object in a pre-scan and acquiring imaging MR signal data from the object in parallel via one or more receiving coils having different spatial sensitivity profiles. The MR signal data are acquired with sub-sampling of k-space and with spectral fat suppression and an MR image is reconstructed from the imaging MR signal data. Sub-sampling artefacts are eliminated using sensitivity maps indicating the spatial sensitivity profiles of the two or more RF receiving coils. A $B_0$ map is derived from the reference MR signal data and the spatial dependence of the effectivity of the spectral fat suppression is determined using the Bo map. In the image reconstruction step, signal contributions from water and fat are separated using regularisation taking the spatial dependence of the effectivity of the spectral fat suppression into account.

20 Claims, 2 Drawing Sheets

(51) Int. Cl.
  *G01R 33/34* (2006.01)
  *G01R 33/56* (2006.01)
  *G01R 33/485* (2006.01)
  *G01R 33/44* (2006.01)
  *A61B 5/055* (2006.01)
  *G01R 33/48* (2006.01)
  *G01R 33/24* (2006.01)
  *G01R 33/563* (2006.01)

(52) U.S. Cl.
  CPC ....... *G01R 33/485* (2013.01); *G01R 33/5607* (2013.01); *G01R 33/5608* (2013.01); *A61B 5/055* (2013.01); *G01R 33/243* (2013.01); *G01R 33/4828* (2013.01); *G01R 33/5615* (2013.01); *G01R 33/5616* (2013.01); *G01R 33/56341* (2013.01)

(58) Field of Classification Search
  USPC ........................................................ 324/309
  See application file for complete search history.

(56) References Cited

U.S. PATENT DOCUMENTS

| | | | |
|---|---|---|---|
| 2004/0013212 A1* | 1/2004 | Benesty | H04L 1/06 375/347 |
| 2010/0201357 A1* | 8/2010 | Ogawa | G01R 33/3808 324/301 |
| 2011/0199084 A1* | 8/2011 | Hasan | A61B 5/055 324/309 |
| 2011/0218253 A1* | 9/2011 | Lange | A61K 45/00 514/789 |
| 2016/0124064 A1* | 5/2016 | de Weerdt | G01R 33/243 324/309 |

* cited by examiner

PARALLEL MR IMAGING WITH SPECTRAL FAT SUPPRESSION

The present application claims priority to EP18160893.6 filed Mar. 9, 2018. This application is hereby incorporated by reference herein.

FIELD OF THE INVENTION

The invention relates to the field of magnetic resonance (MR) imaging. It concerns a method of MR imaging of an object positioned in an examination volume of a MR device. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field $B_0$ whose direction at the same time defines an axis (normally the z-axis) of the co-ordinate system on which the measurement is based. The magnetic field $B_0$ produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field $B_0$ extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field $B_0$, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to an MR image by means of Fourier transformation.

Parallel acquisition techniques for accelerating MR acquisition are well-established. Methods in this category are SENSE (Pruessmann et al., "SENSE: Sensitivity Encoding for Fast MRI", Magnetic Resonance in Medicine 1999, 42 (5), 1952-1962) and SMASH (Sodickson et al., "Simultaneous acquisition of spatial harmonics (SMASH): Fast imaging with radiofrequency coil arrays", Magnetic Resonance in Medicine 1997, 38, 591-603). SENSE and SMASH use sub-sampled k-space data acquisition obtained from multiple RF receiving coils in parallel. In these methods, the (complex) signal data from the multiple coils are combined with complex weightings in such a way as to suppress sub-sampling artefacts (aliasing) in the finally reconstructed MR images. This type of complex array combining is sometimes referred to as spatial filtering, and includes combining which is performed in the k-space domain (as in SMASH) or in the image domain (as in SENSE), as well as methods which are hybrids. In either SENSE or SMASH, it is essential to know the proper weightings or spatial sensitivities of the receiving coils with sufficient accuracy. To obtain the coil sensitivities, i.e. the spatial sensitivity profiles of the receiving coils used for signal detection, a calibration pre-scan is typically performed prior to and/or after the actual image acquisition. In the pre-scan, the MR signals are usually acquired at a resolution which is significantly lower than the resolution required for the diagnostic MR image. The low-resolution pre-scan typically consists of an interleaving of signal acquisition via the array of receiving coils and via a volume coil, for example the quadrature body coil of the MR apparatus. Low resolution MR images are reconstructed from the MR signals received via the array receiving coils and via the volume RF coil. Sensitivity maps indicating the spatial sensitivity profiles of the receiving coils can then computed, for example, by division of the receiving coil images by the volume coil image.

MR imaging is sensitive to diffusion. Known diffusion-weighted imaging (DWI) techniques are commonly performed by using imaging sequences comprising diffusion gradients, wherein the diffusion of protons (of water molecules) along the direction of the diffusion gradient reduces the amplitude of the acquired MR signals. Diffusion tensor imaging (DTI) is a more sophisticated form of DWI, which allows for the determination of both the magnitude and the directionality of diffusion. Diffusion imaging is clinically used, e.g., to detect cancerous tissue. Cancerous lesions show bright signal in diffusion images because of restricted diffusion characterized by a low apparent diffusion coefficient (ADC).

DWI is typically performed using an echo planar imaging (EPI) technique in combination with fat suppression. Therein, spectral fat suppression is performed, e.g., by known SPIR (spectral pre-saturation with inversion recovery) or SPAIR (spectrally attenuated inversion recovery) techniques. The combination of EPI with SENSE parallel imaging is useful to minimize geometry distortions caused by $B_0$ field inhomogeneity (see WO 2014/195384 A1). Reliable fat suppression is of critical importance to minimize unfolding artefacts and resulting errors in the derived ADC values. However, spectral fat suppression is hampered by $B_0$ field inhomogeneity. Inadequate fat suppression at the locations of lesions may impact lesion conspicuity and the obtained ADC values.

SUMMARY OF THE INVENTION

From the foregoing it is readily appreciated that there is a need for an improved MR imaging technique. One aspect of the invention is to provide a method that enables parallel imaging in combination with fat suppression at an increased image quality, notably in combination with EPI.

In accordance with the invention, a method of MR imaging of an object positioned in an examination volume of a MR device is disclosed. The method comprises the steps of:
  acquiring reference MR signal data from the object;
  deriving a $B_0$ map from the reference MR signal data;
  acquiring imaging MR signal data from the object in parallel via one or more receiving coils having different spatial sensitivity profiles, wherein the MR signal data are acquired with sub-sampling of k-space and with spectral fat suppression;
  determining the spatial dependence of the effectivity of the spectral fat suppression using the $B_0$ map; and
  reconstructing a MR image from the imaging MR signal data, wherein sub-sampling artefacts are eliminated using sensitivity maps indicating the spatial sensitivity profiles of the two or more RF receiving coils, wherein signal contributions from water and fat to the imaging MR signal data are separated in the step of reconstructing the MR image using regularisation which takes the spatial dependence of the effectivity of the spectral fat suppression into account.

The invention proposes to use $B_0$ information to determine the spatial dependence of the effectivity of the fat suppression and to constrain the parallel (SENSE) reconstruction accordingly (by regularisation). The approach of the invention improves image quality in applications in which spectral fat suppression is used in combination with SENSE. The invention is especially useful for EPI type of acquisition which suffer from large $B_0$ inhomogeneity-induced distortions. A better and more reproducible image quality will be obtained by the method of the invention in particular in combination with EPI used for DWI or functional MRI.

According to the invention, a parallel imaging (SENSE) scan is performed with spectral fat suppression. $B_0$ information is derived in a reference scan. The $B_0$ information is used to determine the quality and spatial dependence of the fat suppression. A too large $B_0$ non-uniformity will cause fat suppression failure. This insight is exploited according to the invention to improve the image quality, e.g. in terms of signal-to-noise (SNR), as the inverse problem of the image reconstruction will be better conditioned by corresponding regularisation. In image areas with decent spectral fat suppression, SNR is improved compared to the case when conventional parallel image reconstruction would be applied. Compared to the conventional approach applying spectral fat suppression only, less fat suppression artefacts will be observed in MR images produced by the method of the invention.

Fat suppression, as employed according to the invention in combination with parallel imaging, is the process of utilizing specific parameters of the used imaging sequence to remove, to the largest possible extent, the effects of signal contributions from fat protons to the resulting MR image. For example, frequency-selective RF excitation pulses may be applied, which produce saturation of the magnetization of fat protons. Known SPIR or SPAIR techniques may be used for MR signal acquisition in the method of the invention.

Signal contributions from water and fat protons to the imaging MR signal data are separated in the step of reconstructing the MR image, whereby a water image and a fat image are obtained. In other words, the invention enables the simultaneous reconstruction of a water image and a fat image by means of SENSE reconstruction from the acquired imaging MR signal data. Preferably, the water image is reconstructed using a water sensitivity map, and the fat image is reconstructed using a fat sensitivity map that is different from the water sensitivity map. This takes the fat-shift into account. Each of the separate water and fat sensitivity maps accurately represent the sensitivities of the used receiving coils at the locations of water and fat tissue respectively. The fat sensitivity map may be computed from the water sensitivity map by a simple translation in the direction of the fat shift.

Regularisation (as, e.g., regularised SENSE) is used for simultaneous reconstruction of a water image and a fat image from the acquired imaging MR signal data. The application of regularisation is per se known in the art. It is particularly advantageous in cases in which the inverse problem of MR image reconstruction is ill-conditioned, for example due the geometry of the sensitivity maps and/or the applied k-space sampling scheme. Regularisation improves the conditioning of the inverse problem of MR image reconstruction. By using regularisation, the solution of the reconstruction problem is biased towards some prior information which is introduced into the reconstruction algorithm as a corresponding regularisation map. This prior information encompasses, according to the invention, the spatial dependence of the effectivity of the fat suppression over the examined anatomy. It is in principle possible to use one regularisation map for reconstructing both the water and the fat image. However, it turns out that image quality can be significantly improved if suitably selected separate regularisation maps are used for reconstructing the water and fat images. This means that independent regularisations are applied for reconstructing the water and fat images respectively. If, for example, the reference MR signal data are acquired using multi-point Dixon, as described below, the obtained (low-resolution) water map can advantageously be used as a water regularisation map while the fat map can be used as a fat regularisation map. The water and fat maps obtained with the multi-point Dixon method in combination with the determined spatial dependence of the effectivity of the fat suppression provide valuable information regarding the locations of water and fat tissue within the examined anatomy. This information is exploited according to the invention to improve the conditioning of the reconstruction problem and the image quality.

As mentioned before, the reference MR signal data may be advantageously acquired using a multi-point Dixon technique. According to the per se known multi-point Dixon technique, the spectral difference between fat and water protons is made use of for the purpose of separating MR signals emanating from water containing tissue and MR signals emanating from fat tissue. In multi-point Dixon, multiple acquisitions of k-space are repeated with different echo times. The simplest Dixon technique, 2-point Dixon, acquires two complete k-space data sets, wherein the fat magnetization in the second acquisition is out of phase relative to the first acquisition at the respective echo times. Separate and distinct water and fat images are obtained by simple addition or a subtraction of the complex MR signal data sets. In general, a $B_0$ map, a water map and a fat map can be obtained by means of the multi-point Dixon technique. Of particular advantage is that $B_0$ mapping using multi-point Dixon is very fast and provides useful information regarding the water and fat distribution (in the form of water map and a fat map) within the field of view in addition to the $B_0$ map. The $B_0$ map is exploited according to the invention for determining the spatial dependence of the effectivity of the fat suppression. The obtained water and fat maps may be used to derive the water sensitivity maps and fat sensitivity maps attributed to the used RF receiving coils, e.g., by comparing the reference MR signal data acquired in parallel via the (local) RF receiving coils and via a volume (body) RF coil.

Preferably, the reference MR signal data are acquired at an image resolution that is lower than the image resolution of the imaging MR signal data. Because of the reduced image resolution, the reference MR signal data can be acquired much faster than the imaging MR signal data.

According to a preferred embodiment of the invention, the reference MR signal data and/or the imaging MR signal data are acquired using EPI. An adaptation to correct for geometry distortions owing to $B_0$ inhomogeneities may applied to the sensitivity maps like in the above-cited WO 2014/195384 A1. After the correction, the sensitivity maps accurately represent the 'true' sensitivities of the used RF receiving coils at the respective locations of the patient's anatomy. This approach enables to reduce residual sub-sampling artefacts after SENSE reconstruction.

The method of the invention described thus far can be carried out by means of a MR device including at least one main magnet coil for generating a uniform, steady magnetic field $B_0$ within an examination volume, a number of gradient coils for generating switched magnetic field gradients in different spatial directions within the examination volume, at least one RF coil for generating RF pulses within the examination volume, one or more receiving coils for receiving MR signals from an object positioned in the examination volume, a control unit for controlling the temporal succession of RF pulses and switched magnetic field gradients, and a reconstruction unit. The method of the invention is implemented by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
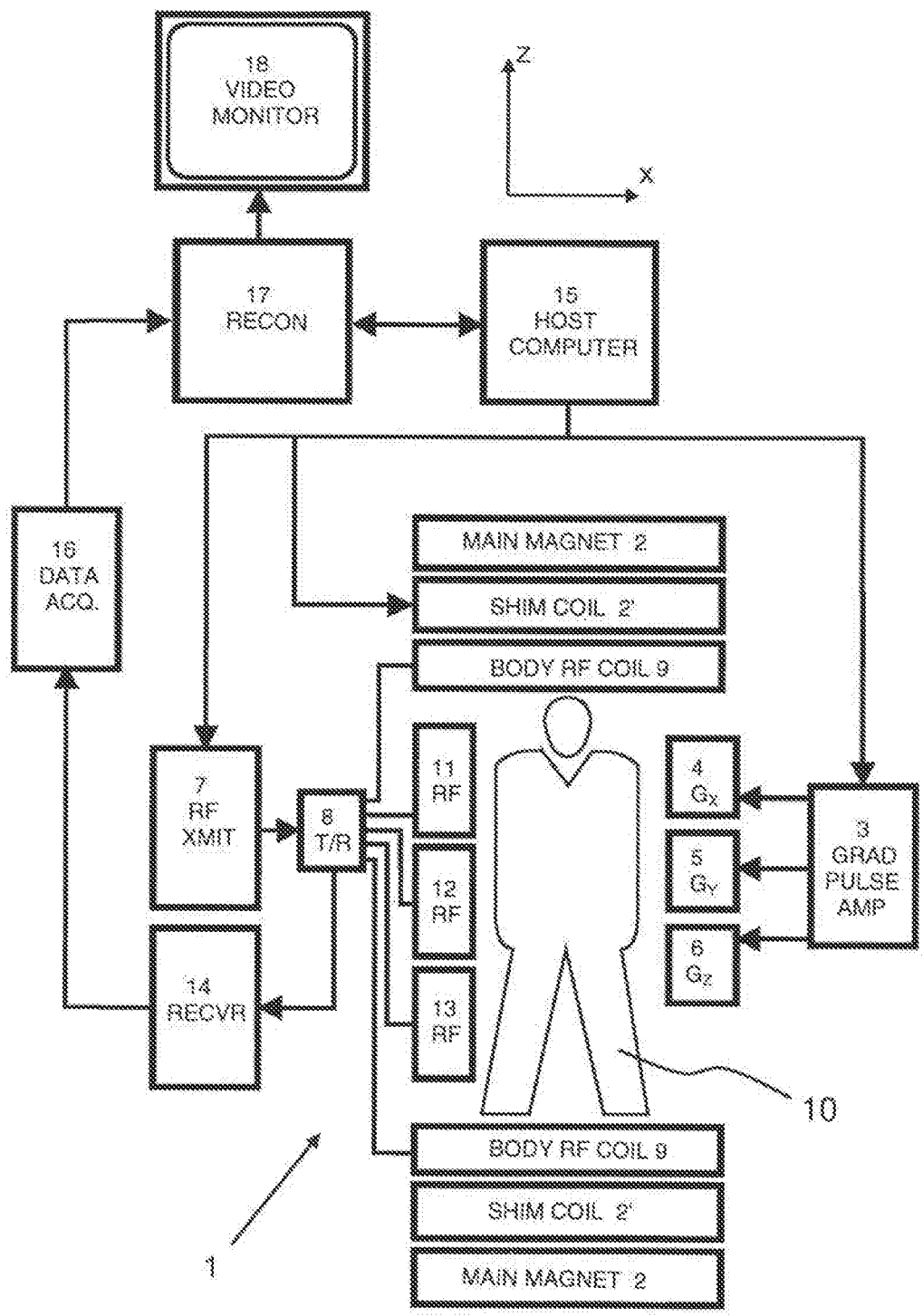
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used as receiving coils to receive MR signals induced by body-coil RF transmissions.

The resultant MR signals are picked up by the body RF coil 9 and/or by the array RF coils 11, 12, 13 and demodulated by a receiver 14 preferably including a pre-amplifier (not shown). The receiver 14 is connected to the RF coils 9, 11, 12 and 13 via send-/receive switch 8.

A host computer 15 controls the shimming coils 2' as well as the gradient pulse amplifier 3 and the transmitter 7 to generate any of a plurality of MR imaging sequences, such as echo planar imaging (EPI). For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices, the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
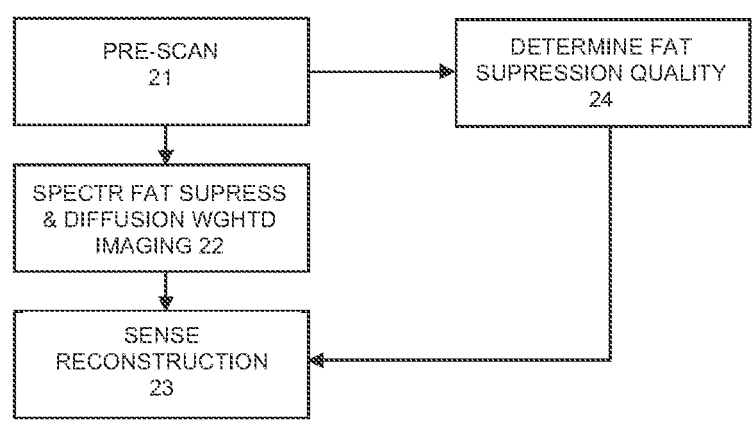
FIG. 2 schematically illustrates the method of the invention as a flow chart.

A practical embodiment of the method of the invention is described with reference to FIG. 2 and with further reference to FIG. 1 as follows:

After positioning the body 10 in the iso-centre of the main magnet coil 2, a pre-scan is started in step 21 for acquiring reference MR signal data. The pre-scan uses interleaving signal acquisition via the body RF coil 9 and the array RF coils 11, 12, 13. Sensitivity maps $CSM_w$ and $CSM_f$ indicating the spatial sensitivity profiles of the array RF coils 11, 12, 13 for fat and water are derived from the reference MR signal data as well as a $B_0$ map. A multi-point Dixon technique is employed for this purpose. The reference MR signal data are acquired at low resolution, i.e. from a limited central portion of k-space. The whole pre-scan can thus be performed within a couple of seconds.

After the pre-scan, an EPI imaging scan with spectral fat suppression and diffusion weighting is performed in step 22 at a higher image resolution, i.e. an image resolution that is sufficient for the respective diagnostic imaging task. Imaging MR signal data are acquired from the body 10 via the array RF coils 11, 12, 13 in parallel with sub-sampling of k-space. Finally, SENSE reconstruction is applied in step 23 to the acquired imaging MR signal data. Therein, sub-sampling artefacts (aliasing) are suppressed using the sensitivity maps obtained from the pre-scan and, finally, an ADC map is derived indicating the spatially resolved apparent diffusion coefficient of water protons in the imaged tissue region.

According to the invention, the $B_0$ map is used in step 24 to determine the fat suppression quality, i.e., the spatial dependence of the effectivity of the spectral fat suppression. A too large non-uniformity of $B_0$ will cause fat suppression failure which is taken into account by the method of the invention. A spatially dependent function $f(B_0)$ is derived from the $B_0$ map indicating the quality of the fat suppression. In a simple case, $f(B_0)$ may be a binary function as:

$$f(B_0) = \begin{cases} \varepsilon, B_0 \leq D \\ 1, B_0 > D \end{cases}, \varepsilon \ll 1$$

In this embodiment, D is a threshold value which is determined in step 24 to indicate from which deviation of $B_0$ on the spectral fat suppression has to be considered as ineffective.

In step 23, a water image and a fat image are reconstructed simultaneously from the acquired MR signal data m by solving a set of linear equations as follows:

$$\begin{bmatrix} CSM_w & CSM_f \\ R_w^{-1/2} & 0 \\ 0 & (R_f f(B_0))^{-1/2} \end{bmatrix} \begin{bmatrix} p_w \\ p_f \end{bmatrix} = \begin{bmatrix} m \\ 0 \\ 0 \end{bmatrix}$$

Therein, m represents the vector of imaging MR signal data for all used receiving coils, $p_w$ and $p_f$ are the vectors of the image values of the water image and the fat image respectively. $CSM_w$ and $CSM_f$ are matrix representations of the sensitivity maps for water and fat for all used receiving coils 11, 12, 13. A regularised SENSE reconstruction scheme is applied. $R_w$ and $R_f$ are the corresponding (diagonal) regularisation matrices for water and fat respectively. The method of the invention may be extended by determining separate functions $f_f(B_0)$ indicating, as $f(B_0)$ above, the quality of the fat suppression, and $f_w(B_0)$ indicating the (unintentional) $B_0$ inhomogeneity-induced suppression of water. In this case, the set of linear equations describing the reconstruction problem reads:

$$\begin{bmatrix} CSM_w & CSM_f \\ (R_w f_w(B_0))^{-1/2} & 0 \\ 0 & (R_f f_f(B_0))^{-1/2} \end{bmatrix} \begin{bmatrix} p_w \\ p_f \end{bmatrix} = \begin{bmatrix} m \\ 0 \\ 0 \end{bmatrix}$$

Water and fat maps derived from the reference MR signal data acquired in step 21 may be used advantageously as regularisation maps $R_w$ and $R_f$ for the reconstruction of the water and fat images respectively. These maps provide valuable information regarding the location of water and fat signal. Hence, using the multi-point Dixon acquisition as a pre-scan enhances conditioning significantly. It has to be noted that the conditioning of the SENSE reconstruction can be improved considerably by the method of the invention. Any signal contribution from fat protons which is not (fully) suppressed can be removed using the proposed technique, thus leading to a very robust fat suppressed SENSE reconstruction and very accurate ADC maps.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of magnetic resonance (MR) imaging of an object positioned in an examination volume of a MR device, the method comprises:
   acquiring reference MR signal data from the object;
   deriving a $B_0$ map from the reference MR signal data;
   acquiring imaging MR signal data from the object in parallel via more than one receiving coils having different spatial sensitivity profiles, wherein the MR signal data are acquired with sub-sampling of k-space and with spectral fat suppression;
   determining the spatial dependence of the effectivity of the spectral fat suppression using the $B_0$ map; and
   reconstructing an MR image from the imaging MR signal data, wherein subsampling artefacts are eliminated using sensitivity maps indicating the spatial sensitivity profiles of the two or more RF receiving coils wherein signal contributions from water and fat to the imaging MR signal data are separated in the step of reconstructing the MR image using regularization which takes the spatial dependence of the effectivity of the spectral fat suppression into account.

2. The method of claim 1, wherein the reference MR signal data are acquired using a multi-point Dixon technique.

3. The method of claim 2, wherein signal contributions from water and fat to the reference MR signal data are separated, whereby a water sensitivity map and a fat sensitivity map are derived from the reference MR signal data.

4. The method of claim 3, wherein the fat sensitivity map is computed from the water sensitivity map by a translation in the direction of a fat shift.

5. The method of claim 1, wherein the reference MR signal data are acquired at an image resolution that is lower than the image resolution of the imaging MR signal data.

6. The method of claim 1, wherein the reference MR signal data and/or the imaging MR signal data are acquired by using echo planar imaging.

7. The method of claim 1, wherein the imaging MR signal data are diffusion weighted.

8. A magnetic resonance device (MR) device comprising:
at least one main magnet coil for generating a uniform, steady magnetic field $B_0$ within an examination volume,
a plurality of gradient coils for generating switched magnetic field gradients in different spatial directions within the examination volume,
at least one RF coil for generating RF pulses within the examination volume, more than one receiving coils for receiving MR signals from an object positioned in the examination volume,
a control unit for controlling the temporal succession of RF pulses and switched magnetic field gradients, and a reconstruction unit, wherein the MR device is configured to:
acquire reference MR signal data from the object;
derive a $B_0$ map from the reference MR signal data;
acquire imaging MR signal data from the object in parallel via one or more receiving coils having different spatial sensitivity profiles, wherein the MR signal data are acquired with sub-sampling of k-space and with spectral fat suppression;
determine the spatial dependence of the effectivity of the spectral fat suppression using the $B_0$ map; and
reconstruct an MR image from the imaging MR signal data, wherein subsampling artefacts are eliminated using sensitivity maps indicating the spatial sensitivity profiles of the two or more RF receiving coils wherein signal contributions from water and fat to the imaging MR signal data are separated in the step of reconstructing the MR image using regularization which takes the spatial dependence of the effectivity of the spectral fat suppression into account.

9. A computer program stored on a non-transitory computer readable medium carrying software configured to run a magnetic resonance (MR) device to perform the method of claim 1.

10. One or more computer processors configured to control a magnetic resonance device to perform the method of claim 1.

11. A method of magnetic resonance (MR) imaging of an object positioned in an examination volume of a MR device, the method comprising:
acquiring reference MR signal data from the object;
deriving a $B_0$ map from the reference MR signal data;
acquiring imaging MR signal data from the object in parallel via more than one receiving coils having different spatial sensitivity profiles, wherein the MR signal data are acquired with sub-sampling of k-space and with spectral fat suppression;
determining the spatial dependence of the effectivity of the spectral fat suppression using the $B_0$ map; and
reconstructing an MR image from the imaging MR signal data, wherein subsampling artefacts are eliminated using sensitivity maps indicating the spatial sensitivity profiles of the two or more RF receiving coils wherein signal contributions from water and fat to the imaging MR signal data are separated in the step of reconstructing the MR image using regularization which takes the spatial dependence of the effectivity of the spectral fat suppression into account;
wherein reconstructing the MR image includes simultaneously reconstructing water and fat images with a SENSE reconstruction by solving a set of linear equations:

$$\begin{bmatrix} CSM_w & CSM_f \\ R_w^{-1/2} & 0 \\ 0 & (R_f f(B_0))^{-1/2} \end{bmatrix} \begin{bmatrix} p_w \\ p_f \end{bmatrix} = \begin{bmatrix} m \\ 0 \\ 0 \end{bmatrix}$$

where $CSM_w$ is a matrix representation of the spatial sensitivity map for water, $CSM_f$ is a matrix representation of the spatial sensitivity map for fat, $R_w$ is a diagonal regularization matrix for water and $R_f$ is a diagonal regularization matrix for fat, $f(B_0)$ is a spatially dependent function indicative of a quality of the fat suppression, $p_w$ and $p_f$ are vector values of the water image and the fat image respectively, and m is a vector representation of the imaging MR signal data.

12. The method of claim 11, wherein determining the spectral dependence of the spectral fat suppression includes determining the function $f(B_0)$ of the $B_0$ field where $$f(B_0) = \begin{cases} \varepsilon, & B_0 \leq D \\ 1, & B_0 > D \end{cases}, \varepsilon \ll 1$$

where D is a threshold value indicative of a deviation of $B_0$ in which the spectral fat suppression is ineffective.

13. A method of magnetic resonance (MR) imaging of an object positioned in an examination volume of a MR device, the method comprising:
acquiring reference MR signal data from the object;
deriving a $B_0$ map from the reference MR signal data;
acquiring imaging MR signal data from the object in parallel via more than one receiving coils having different spatial sensitivity profiles, wherein the MR signal data are acquired with sub-sampling of k-space and with spectral fat suppression;
determining the spatial dependence of the effectivity of the spectral fat suppression using the $B_0$ map; and
reconstructing an MR image from the imaging MR signal data, wherein subsampling artefacts are eliminated using sensitivity maps indicating the spatial sensitivity profiles of the two or more RF receiving coils wherein signal contributions from water and fat to the imaging MR signal data are separated in the step of reconstructing the MR image using regularization which takes the spatial dependence of the effectivity of the spectral fat suppression into account;
wherein reconstructing the MR image includes simultaneously reconstructing water and fat images by solving a set of linear equations:

$$\begin{bmatrix} CSM_w & CSM_f \\ (R_w f_w(B_0))^{-1/2} & 0 \\ 0 & (R_f f_f(B_0))^{-1/2} \end{bmatrix} \begin{bmatrix} p_w \\ p_f \end{bmatrix} = \begin{bmatrix} m \\ 0 \\ 0 \end{bmatrix}$$

where $CSM_w$ is a matrix representation of the spatial sensitivity map for water, $CSM_f$ is a matrix representation of the spatial sensitivity map for fat, $R_w$ is a diagonal regularization matrix for water and $R_f$ is a diagonal regularization matrix for fat, $f(B_0)$ is a spatially dependent function indicative of a quality of the fat suppression, $p_w$ and $p_f$ are vector values of the water image and the fat image respectively, and m is a vector representation of the imaging MR signal data.

14. The method according to claim 3, wherein the water and fat sensitivity maps are used for water and fat regularization matrices, respectively, during the step of reconstructing the MR image to account for the spatial dependence of the effectivity of the spectral fat suppression.

15. The method of claim 1, wherein determining the spatial dependence of the efficacy of the spectral fat suppression includes generating water and fat maps from the acquired reference magnetic signal data.

16. The method of claim 15, wherein reconstructing the MR image includes applying diagonal regularization matrices for fat and water based on the water and fat maps generated from the reference MR signal data.

17. The method of claim 13, wherein the MR image is reconstructed using SENSE reconstruction.

18. The method of claim 17, further including generating an apparent diffusion coefficient indicating a spatially resolved apparent diffusion coefficient of water protons in the imaged tissue region.

19. A method of magnetic resonance (MR) imaging of an object positioned in an examination region of an MR device, the method comprising:

from reference MR signal data acquired from an array of RF coils in a pre-scan, generating sensitivity maps indicating spatial sensitivity profiles of the array of RF coils for fat and water, the reference RF scan data being acquired at a low resolution from a limited central portion of k-space;

after the pre-scan, performing an imaging scan with spectral fat suppression and diffusion weighting at a higher resolution in parallel with sub-sampling of k-space;

applying a SENSE reconstruction technique to the acquired imaging MR signal data, sub-sampling artifacts being suppressed using the sensitivity maps obtained from the pre-scan, and deriving an apparent diffusion coefficient map indicating a spatially resolved apparent diffusion coefficient of water protons in the imaged tissue region;

using the $B_0$ map to determine a spatial dependence of an effectivity of the spectral fat suppression including deriving a spatially dependent function $f(B_0)$ from the $B_0$ map indicating the quality of the fat suppression;

wherein, in the SENSE reconstruction, the water and fat maps generated in the pre-scan from the reference MR signal data are used as diagonal regularization maps for the reconstruction of the water and fat images respectively.

20. One or more computer processors programmed to perform the method of claim 19.

* * * * *